United States Patent [19]

Weber et al.

[11] Patent Number: 4,732,900
[45] Date of Patent: Mar. 22, 1988

[54] 1,2,4-TRIAZOLO-CARBAMATES

[75] Inventors: Karl-Heinz Weber, Gau-Algesheim; Dieter Hinzen, Zornheim; Franz-Josef Kuhn, Gau-Algesheim; Erich Lehr, Waldalgesheim; Wilhelm Frölke, Ingelheim am Rhein; Wolfgang Tröger, Stromberg; Helmut Ensinger, Wackernheim; Gerhard Walther, Bingen; Albrecht Harreus, Ingelheim am Rhein, all of Fed. Rep. of Germany

[73] Assignee: Boehringer Ingelheim KG, Ingelheim am Rhein, Fed. Rep. of Germany

[21] Appl. No.: 791,184

[22] Filed: Oct. 25, 1985

[30] Foreign Application Priority Data

Oct. 27, 1984 [DE] Fed. Rep. of Germany ....... 3439450

[51] Int. Cl.⁴ ............... C07D 249/12; C07D 401/12; C07D 401/14; A61K 31/41
[52] U.S. Cl. ............................... 514/255; 514/340; 514/384; 544/366; 546/276; 548/263
[58] Field of Search ............ 548/263; 546/276; 544/366; 514/384, 340, 255

[56] References Cited

U.S. PATENT DOCUMENTS

| | | | |
|---|---|---|---|
| 4,156,085 | 5/1979 | Baldwin et al. | 546/276 |
| 4,160,839 | 7/1979 | Kirkpatrick | 548/263 |
| 4,209,515 | 6/1980 | Heckendorn et al. | 544/366 |
| 4,578,479 | 3/1986 | Fukui et al. | 544/366 |
| 4,610,717 | 9/1986 | Mansuri et al. | 548/263 |

OTHER PUBLICATIONS

Sunderdiek et al., CA 81:91438k (1974).
Hoyer et al., CA 87:68245k (1977).

Primary Examiner—Glennon H. Hollrah
Assistant Examiner—D. L. Dinner
Attorney, Agent, or Firm—David E. Frankhouser; Alan R. Stempel; Mary Ellen M. Timbers

[57] ABSTRACT

New 1,2,4-triazolo-carbamates of general formula

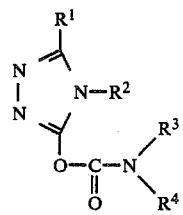

I wherein $R^1$, $R^2$, $R^3$ and $R^4$ have the meanings given in the specification, are acetylcholinesterase inhibitors and may be used as drugs for the treatment of senile dementia.

10 Claims, No Drawings

1,2,4-TRIAZOLO-CARBAMATES

The invention relates to new 1,2,4-triazolo-carbamates and the acid addition salts thereof, therapeutic methods of using them and pharmaceutical compositions which contain these compounds.

The new compounds are capable of counteracting the restriction of the short-term memory after the administration of muscarinic cholinergic antagonists. In senile dementia of the Alzheimer's disease type, which goes along a depletion of acetylcholine in the central nervous system, the new compounds may be used as potential drugs for treating this syndrome, since they inhibit central acetylcholinesterase in a long-lasting but reversible manner. Known acetylcholinesterase inhibitors, e.g. alkylphosphates, physostigmin, neostigmin, pyridostigmin, etc., have considerable peripheral side effects and are highly toxic, in some cases incapable of acting on the brain, or their activity is either too short or too long, thus rendering therapeutic use in humans either very difficult or impossible.

The invention relates to new 1,2,4-triazolo-carbamates of general formula

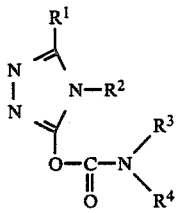

I wherein
$R^1$ represents hydrogen, a straight-chained or branched alkyl group with 1 to 8 carbon atoms, a 3 to 6-membered carbocyclic ring, a benzyl or phenethyl group;
$R^2$ represents a phenyl or pyridinyl group which may be mono- or disubstituted by halogen, methyl, methoxy or trifluoromethyl;
$R^3$ and $R^4$, which may be identical or different, represent hydrogen, a straight-chained or branched alkyl group with 1 to 6 carbon atoms, a cycloalkyl group with 3 to 6 carbon atoms, an aryl or heteroaryl group optionally substituted by halogen, methoxy or trifluoromethyl or by a straight-chained or branched alkyl group with 1 to 6 carbon atoms, $R^3$ and $R^4$ together with the nitrogen atom may represent a saturated 5- or 6-membered ring, optionally substituted by one or more straight-chained or branched alkyl groups with 1 to 4 carbon atoms, whilst this 5- or 6-membered ring may contain, as a further heteroatom, nitrogen, oxygen or sulphur and, in the case of nitrogen, this may be substituted with an alkyl group with 1 to 4 carbon atoms or a hydroxyalkyl group with 1 to 3 carbon atoms,
and the physiologically acceptable acid addition salts thereof.

Unless otherwise stated, halogen may represent F, Cl, Br or I; the preferred aryl group is phenyl, whilst preferred heteroaryl groups are pyridine and pyrazine.

The compounds of general formula I may optionally be converted by known methods to their physiologically acceptable acid addition salts.

Suitable acids for this include both inorganic acids such as hydrohalic acids, sulphuric, phosphoric and aminosulphonic acid, and also organic acids such as formic, acetic, propionic, lactic, glycolic, gluconic, maleic, fumaric, succinic, tartaric, benzoic, salicylic, citric, ascorbic or p-toluenesulphonic acid or oxyethanesulphonic acid.

Preferred compounds of general formula I are those wherein $R^1$ represents a methyl or ethyl group, $R^2$ represents a chlorine-substituted phenyl or pyridinly group; $R^3$ represents hydrogen or a methyl or ethyl group, $R^4$ represents a lower alkyl group with 1 to 4 carbon atoms, or $R^3$ and $R^4$ together with the nitrogen represents an N-methyl-substituted piperazinyl group, such as, for example:
4-(5-Chloropyridin-2-yl)-3-methyl-5-[(4-methyl-piperazinyl)carbonyl]oxy-1,2,4-triazole,
4-(5-Chloropyridin-2-yl)-3-methyl-5-[N-tert.-butylaminocarbonyl]oxy-1,2,4-triazole,
4-(4-Chlorophenyl)-3-ethyl-5-[(4-methylpiperazinyl)-carbonyl]oxy-1,2,4-triazole,
4-(5-Chloropyridin-2-yl)-3-methyl-5-[N,N-diethylaminocarbonyl]oxy-1,2,4-triazole,
4-(5-Chloropyridin-2-yl)-3-methyl-5-[N-methylaminocarbonyl]oxy-1,2,4-triazole,
4-(5-Chloropyridin-2-yl)-3-methyl-5-[N,N-dimethylaminocarbonyl]oxy-1,2,4-triazole,
4-(4-Chlorophenyl)-3-methyl-5-((4-methylpiperazinyl)-carbonyl]oxy-1,2,4-triazole.

The compounds of formula I can be prepared by several methods.

Starting from 5-hydroxy-1,2,4-triazoles of general formula

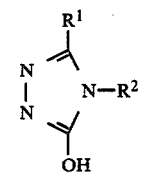

II wherein
$R^1$ and $R^2$ are as hereinbefore defined, the compounds of general formula I are obtained by reacting 5-hydroxytriazoles of general formula II, optionally with the addition of bases, with a halocarbonylamide of general formula

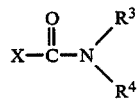

III wherein
$R^3$ and $R^4$ are as hereinbefore defined and X represents a halogen, preferably chlorine. A compound of general formula II is either reacted with a halocarbonylamide of general formula III, appropriately with the addition of a tertiary organic base, such as triethylamine or pyridine, or in the presence of another base, or compounds of general formula II are converted into the salts thereof with bases and these salts are reacted with a halocarbonylamide of general formula III. In general it is not necessary to isolate the salts.

Preferred bases include alkaline and alkaline earth metal hydrides such as sodium hydride or calcium hydride, alkoxides such as sodium methoxide, sodium ethoxide, sodium isopropoxide, potassium tert.butoxide or aluminium isopropoxide.

The reaction is preferably carried out using an organic solvent at between 0° C. and the boiling point of the solvent, with moisture being excluded. Suitable solvents include ether, cyclic ethers such as tetrahydrofuran or dioxane, suitable halogenated hydrocarbons such as methylene chloride, acetonitrile, dimethylformamide, dimethylsulphoxide, toluene or benzene.

Another method of preparing compounds of general formula I consists in reacting compounds of general formula II, optionally with the addition of bases, with a suitable halocarbonate of general formula

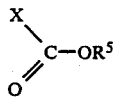   IV wherein
X is as hereinbefore defined and $R^5$ represents an alkyl or aryl group which is suitable as a leaving group, and subsequently reacting with a primary or secondary amine of general formula

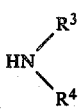   V wherein
$R^3$ and $R^4$ are as hereinbefore defined.

A compound of general formula II is reacted with a suitable halocarbonate of general formula IV wherein $R^5$ preferably represents a phenyl, nitrophenyl or benzyl group, optionally with the addition of a tertiary organic auxiliary base such as triethylamine or pyridine, or another base, or else the compound of general formula II is converted with bases into the salts thereof and reacted with halocarbonates.

Preferred bases are alkaline and alkaline earth metal hydrides such as sodium hydride or calcium hydride, alkoxides such as sodium methoxide, sodium ethoxide, sodium isopropoxide, potassium tert.butoxide or aluminium isopropoxide.

The reaction of II or the salts thereof with IV is preferably carried out in an inert organic solvent such as ether, cyclic ethers such as tetrahydrofuran or dioxan, suitable halogenated hydrocarbons such as methylene chloride, acetonitrile, dimethylformamide, dimethylsulpoxide, toluene or benzene, at between 0° C. and the boiling point of the solvent whilst moisture is excluded.

The triazolocarbonates formed as intermediate products in the reaction may be isolated or further reacted in situ. When they are treated with primary or secondary amines the corresponding end products of general formula I are obtained.

The reaction may be carried out in one of the above-mentioned solvents or without a solvent in an excess of the amine, the temperatures are between −20° C. and the boiling point of the solvent, whilst the individual reaction conditions will depend on the basicity and boiling point of the amine. In the case of low boiling amines, the reaction may, under certain circumstances, have to be carried out in an autoclave.

Another method of preparing compounds of general formula I is by reacting compounds of general formula II, with the addition of bases, with carbamidic acid esters of general formula

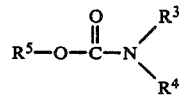   VI wherein
$R^3$, $R^4$ and $R^5$ are as hereinbefore defined.

The triazole II is converted into a corresponding salt by the addition of a base and then reacted with the ester VI. It is not absolutely essential to isolate the salt. Suitable inert solvents include ether, cyclic ethers such as tetrahydrofuran or dioxan, suitable halogenated hydrocarbons such as methylene chloride, acetonitrile, dimethylformamide, dimethylsulphoxide, toluene or benzene.

The preferred bases are alkaline and alkaline earth metal hydrides, such as sodium hydride or calcium hydride, alkoxides such as sodium methoxide, sodium ethoxide, sodium isopropoxide, potassium tert.butoxide or aluminium isopropoxide. The reaction is preferably carried out with the exclusion of moisture at a temperature between 0° C. and the boiling point of the solvent.

Compounds of general formula I wherein $R^3$ represents hydrogen are obtained by reacting compounds of general formula II, optionally with the addition of bases, with suitable isocyanates of general formula $$O=C=N-R^4$$   VII wherein
$R^4$ is as hereinbefore defined.

A compound of general formula II is reacted with the isocyanate, optionally with the addition of a tertiary organic auxiliary base such as triethylamine or pyridine or another base, or else a compound of general formula II may be converted into the salts thereof with bases and reacted with the isocyanate VII. In general, it is not necessary to isolate the salts.

The reactions are preferably carried out in inert solvents such as ethers, cyclic ethers such as tetrahydrofuran, dioxan, suitable halogenated hydrocarbons such as methylene chloride, acetonitrile, dimethylformamide, dimethylsulphoxide, benzene or toluene at between −50° C. and the boiling point of the solvent, with the exclusion of moisture.

If compounds of general formula II are converted into the salts thereof with the addition of alkoxides, higher boiling solvents such as dioxan may be used in order to distil off the resulting alcohol azeotropically before adding the carbamate-forming component, e.g. chlorocarbonate.

The starting materials for the processes described hereinbefore are known from the literature in some cases or may be prepared using methods known per se.

For example, 5-hydroxy-1,2,4-triazoles in which $R^2$ is a pyridyl group may be prepared by the following method of synthesis.

The reaction of substituted 2-aminopyridines with ethyl orthoformate leads to the corresponding imidoethylesters (1). Cyclisation to form a 1,2,4-triazole derivative (2) is effected by heating with acetioc acid hydrazide in a higher boiling solvent such as diglyme.

Subsequent bromination with bromine or N-bromosuccinimide produces the bromine derivative (3), which can then be hydrolysed to form a 5-hydroxy-1,2,4-triazole of general formula II.

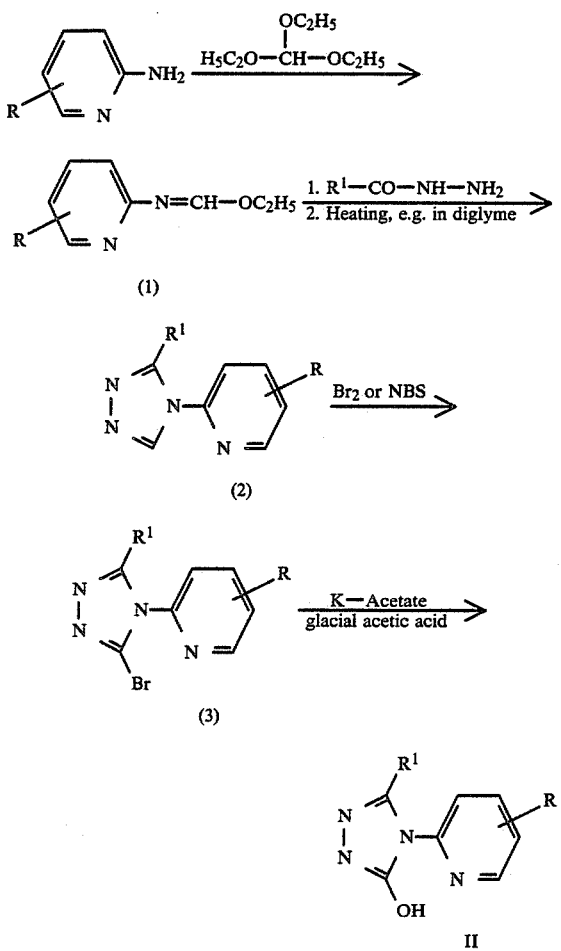

In pharmacological tests using experimental animals, the new compounds demonstrated
- reversible inhibition of central nervous system acetylcholinesterase.
- an improvement in the central nervous system cortical waking reaction.
- a significant increase in the proportion of REM sleep without affecting the overall pattern of sleep,
- activation of the discharging frequency of central cholinergic nerve cells.
- a promotion of learning and memory performance,
- an improvement of the transfer of the contents of the short-term memory into the long-term memory after it has previously been blocked by means of the muscarinic cholinergic antagonist scopolamine.

The above mentioned tests concerning the inhibition of central acetylcholinesterase were carried out by the method of L. Potter, described in *J. Pharmacological Exp. Thes.*, 156, 500 (1967). Compounds of the invention were found to have IC$_{50}$-values (the concentration of the test compound at which hydrolysis of acetylcholinesterase is reduced by about 50%) from about $10^{-30}$ to $10^{-7}$ mol/l, while piracetam had an IC$_{50}$ greater than $10^{-3}$ mol/l.

The above mentioned tests concerning the ability of the new compounds to counteract or reverse the scopolamine induced impairment of the transfer of short-term memory into long-term memory were carried out using the procedure described in *Pharmacology*, 78, 104 (1968). In at least 50% of the test animals a dosage between 5 and 50 mg/kg of the compounds of invention reversed the disruptive effect of scopolamine, while in the case of Piracetam there was no effect at a dosage of 50 mg/kg and the 50% value was obtained only at 100 mg/kg.

By comparison with known acetylcholinesterase inhibitors, the compounds according to the invention have very low toxicity and no harmful peripheral side effects.

Since the depletion of the chemical messenger substance acetylcholine in the brain constitutes a major characteristic of senile degenerative dementia of the Alzheimer's disease type and since this syndrome is accompanied by severe impairment of cognitive and memory performances, the new compounds may be used as drugs for treating symptoms of this syndrome.

The new compounds may also be used for treating cerebral blood flow deficiency, organic brain syndrome, and organic brain disorders.

The new compounds may be used on their own or combined with other active substances according to the invention, and possibly also together with other pharmacologically active substances, e.g., cerebroactivators. Suitable forms for administration include tablets, capsules, suppositories, solutions, syrups, emulsions or dispersible powders. Tablets may be prepared, for example, by mixing the active substance or substances with known excipients, e.g., inert diluents such as calcium carbonate, calcium phosphate or lactose, disintegrants such as corn starch or alginic acid, binders such as starch or gelatine, lubricants such as magnesium stearate or talc, and/or agents for obtaining delayed release such as carboxypolymethylene, carboxymethylcellulose, cellulose acetate phthalate or polyvinylacetate. The tablets may also consist of several layers.

Coated tablets may be prepared in a similar way by coating cores produced analogously to the tablets with substances conventionally used for tablet coatings, e.g. collidone or shellac, gum arabic, talc, titanium dioxide or sugar. In order to obtain delayed release or avoid incompatibilities the core may also consist of several layers. Similarly, the tablet coating may consist of several layers in order to obtain a delayed effect, and the excipients mentioned for the tablets above may be used.

Syrups of the active substances or combinations of active substances according to the invention may additionally contain a sweetener such as saccharin, cyclamate, glycerol or sugar and a flavour improving agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoate.

Injection solutions are prepared in the usual way, e.g. by adding preservatives such as p-hydroxybenzoates or stabilisers such as alkali metal salts of ethylenediaminetetraacetic acid and are then transferred into injection vials or ampoules.

Capsules containing one or more active substances or combinations of active substances may, for example, be prepared by mixing the active substances with inert carriers such as lactose or sorbitol and encapsulating them in gelatine capsules.

Suitable suppositories may be prepared, for example, by mixing with carriers provided for this purpose, such as neutral fats or polyethylene glycol or the derivatives thereof.

The following Examples illustrate the invention without restricting its scope:

EXAMPLE 1

4-(5-Chloropyridin-2-yl)-3-methyl-5-[(4-methylpiperazin-1-yl)carbonyl]oxy-1,2,4-triazole 50 g (0.24 mol) of 4-(5-chloropyridin-2-yl)-5-hydroxy-3-methyl-1,2,4-triazole are dissolved or suspended in 1 litre of absolute tetrahydrofuran. The sodium hydride, degreased with toluene, is added thereto from 10.8 g of a 55% sodium hydride dispersion and the mixture is stirred for 1 hour at ambient temperature. Then 39 g (0.24 mol) of freshly distilled 1-chlorocarbonyl-4-methyl-piperazine (Bp$_{17}$: 120°–124° C.) are added dropwise thereto and the mixture is stirred for a further 5 hours whilst moisture is excluded. The resulting suspension is concentrated by evaporation in vacuo and the residue is carefully mixed with water and neutralised. The solution containing the carbamate is extracted several times with methylene chloride and the organic phase is washed with water, dried and concentrated. The residue is triturated with ether and 55 g (68% of theory) of the title compound are obtained in the form of crystals, m.p. 121°–122° C.

12.5 g of this base are dissolved in 100 ml of methanol and 4.3 g of fumaric acid are added hot. On cooling, the hemifumarate crystallises out, m.p. 173°–175° C. (yield: 17 g). The compound is highly water-soluble; pH of the solution 3.5.

The starting compound, 4-(5-chloropyridin-2-yl)-5-hydroxy-3-methyl-1,2,4-triazole, is obtained as follows:

(a) 81.6 g (0.64 mol) of finely ground 2-amino-5-chloropyridine and 0.6 g of the hydrochloride thereof are heated with 224 g (1.5 mol) of ethyl orthoformate in an oil bath to 130°–140° C. and the resulting ethanol is distilled off. This takes about 5 to 6 hours. 96 g (1.3 mol) of acetic acid hydrazide and 1.8 liters of ethanol are added to the resulting solid residue and the mixture is refluxed for a further 6 hours. After cooling, 82 g of crystals are obtained, m.p. 213°–215° C.

(b) 81.2 g (0.38 mol) of this compound are suspended in 1.5 l of diglyme and heated to 120° C. Then 96 ml of pyridine are added and the mixture is heated to 140°–145° C. for 20–25 hours. 1.4 l of diglyme are then distilled off in vacuo and the cooled residue is mixed with 1.7 l of petroleum ether, whereupon the triazole derivative crystallises out. After suction filtering, 62 g of the desired triazole are obtained in the form of crystals, m.p. 128°–130° C.

(c) 61.7 g (0.32 mol) of this substance are dissolved in 720 ml of methylene chloride and 26 ml (0.32 mol) of pyridine are added. 16.3 ml (0.32 mol) of bromine are added with stirring at ambient temperature and the resulting mixture is stirred for 5 to 7 hours. The reaction mixture is washed with water. Then the methylene chloride phase is dried and concentrated by evaporation. The residue is recrystallised from ethyl acetate and 41 g of the bromine compound are obtained in the form of crystals, m.p. 150°–153° C.

(d) 21.6 g (0.08 mol) of the bromine compound are refluxed in 200 ml of glacial acetic acid and 33.2 g of potassium acetate for 1–2 hours. The mixture is cooled, 200 ml of water are added, the crystals precipitated are suction filtered and then washed with water. Yield 14 g, m.p. 214°–216° C.

EXAMPLE 2

4-(5-Chloropyridin-2-yl)-3-methyl-5-(N-tert.-butylaminocarbonyl) oxy-1,2,4-triazole 19.6 g (0.09 mol) of 4-(5-chloropyridin-2-yl)-5-hydroxy-3-methyl-1,2,4-triazole are suspended in 600 ml of absolute tetrahydrofuran. The mixture is heated to boiling and 20 g (0.2 mol) of tert-butylisocyanate are added, the mixture is heated for 10 minutes and 4 ml of a 5% methanolic sodium methoxide solution are added to the reaction mixture. It is then stirred for 24 hours under reflux conditions, then the suspension is concentrated and the residue is dissolved in methylene chloride and the insoluble components are removed by suction filtering. The organic phase is washed successively with 2 N hydrochloric acid, with sodium hydrogen carbonate solution and with water, dried with magnesium sulphate and evaporated in vacuo. After the addition of ether, 25 g (87% of theory) of the title compound were isolated in the form of crystals, m.p. 132°–134° C.

The following carbamates were also obtained in this way or by a similar method:

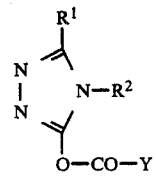

| Example | R$^1$ | R$^2$ | Y | Mp. °C. |
|---|---|---|---|---|
| 3 | H | ![pyridine-Cl] | —N(piperazine)N—CH$_3$ | 167–168 |
| 4 | ![cyclohexyl-H] | ![pyridine-Cl] | —N(piperazine)N—CH$_3$ | 177–178 |

-continued

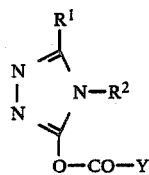

| Example | R¹ | R² | Y | Mp. °C. |
|---|---|---|---|---|
| 5 | —CH₃ | 2-methyl-5-chloropyridin-yl | —NH—CH₃ | 155–156 |
| 6 | —CH₃ | 2-methyl-5-chloropyridin-yl | —N(CH₃)₂ | 151–152 |
| 7 | —CH₃ | 4-chlorophenyl | 4-methylpiperazin-1-yl | 154–156 |
| 8 | —CH₃ | 4-methoxyphenyl | 4-methylpiperazin-1-yl | 128–129 |
| 9 | cyclohexyl (H) | 4-chlorophenyl | 4-methylpiperazin-1-yl | Fu: 158–160 |
| 10 | cyclohexyl (H) | 4-chlorophenyl | —NH—C(CH₃)₃ | 169–170 |
| 11 | —CH(CH₃)₂ | 4-chlorophenyl | 4-methylpiperazin-1-yl | Fu: 204–205 |
| 12 | cyclohexyl (H) | 4-chlorophenyl | —NH—CH₃ | 186–187 |
| 13 | —CH(CH₃)₂ | 4-chlorophenyl | —NH—C(CH₃)₃ | 184–185 |
| 14 | —CH(CH₃)₂ | 3-trifluoromethylphenyl | 4-methylpiperazin-1-yl | Fu: 161–162 |
| 15 | —CH(CH₃)₂ | 4-methoxyphenyl | 4-methylpiperazin-1-yl | Fu: 174–175 |

-continued

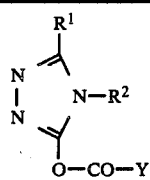

| Example | R¹ | R² | Y | Mp. °C. |
|---|---|---|---|---|
| 16 | —CH₃ | 4-Cl-phenyl | —NH—C(CH₃)₃ | 160–161 |
| 17 | —CH₃ | 4-pyridyl | 4-methylpiperazin-1-yl | Fu: 124–125 |
| 18 | —CH₃ | 3-Cl-pyridin-2-yl | —N(C₂H₅)₂ | 135–136 |
| 19 | —CH₃ | 3-Cl-pyridin-2-yl | —NH—(4-Cl-phenyl) | 176–177 |
| 20 | —CH₃ | 3-Cl-pyridin-2-yl | 2,6-dimethylpiperidin-1-yl | 101–103 |
| 21 | —CH₃ | 3-CF₃-phenyl | 4-methylpiperazin-1-yl | 123–124 |
| 22 | —CH₂—CH₃ | 4-Cl-phenyl | 4-methylpiperazin-1-yl | 192–193 |

Fu = Fumarate

Pharmaceutical Formulation Examples

| (A) Tablets | per tablet |
|---|---|
| Active substance | 100 mg |
| Powdered lactose | 140 mg |
| Corn starch | 240 mg |
| Polyvinylpyrrolidone | 15 mg |
| Magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granulate, the remaining corn starch and the magnesium stearate are screened and mixed together.

The mixture is compressed to form tablets of a suitable size and shape.

| (B) Tablets | per tablet |
|---|---|
| Active substance | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and processed with the remaining corn starch and water to form a granulate which is dried and screened. Then the sodium carboxymethyl starch and the magnesium stearate are added, mixed together and the mixture is compressed to form tablets of a suitable size.

| (C) Ampoules | |
|---|---|
| 4-(5-Chloropyridin-2-yl)-3-methyl-5-[(4-methyl-piperazin-1-yl)carbonyl]oxy-1,2,4-triazole fumarate | 50.0 mg |
| Sodium chloride | 10.0 mg |
| Doubly distilled water q.s. ad | 1.0 ml |

PREPARTATION

The active substance and the sodium chloride are dissolved in doubly distilled water and the solution is decanted into ampoules under sterile conditions.

| (D) Drops | |
|---|---|
| 4-(5-Chloropyridin-2-yl)-3-methyl-5-[(4-methyl-piperazin-1-yl)carbonyl]oxy-1,2,4-triazole fumarate | 5.0 g |
| Methyl p-hydroxybenzoate | 0.1 g |
| Propyl p-hydroxybenzoate | 0.1 g |
| Demineralised water q.s. ad | 100.0 ml |

PREPATATION

The active substance and preservatives are dissolved in demineralised water and the solution is filtered and transferred into vials each containing 100 ml.

What is claimed is:

1. A 1,2,4-triazolo-carbamate of the formula

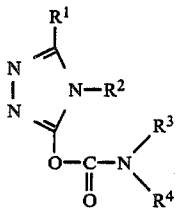

I wherein
$R^1$ is hydrogen, a straight-chained or branched alkyl group with 1 to 8 carbon atoms, a 3 to 6-membered carbocyclic ring, a benzyl or phenethyl group;
$R^2$ is a phenyl or pyridinyl group which may be mono- or disubstituted by halogen, methyl, methoxy or trifluoromethyl;
$R^3$ and $R^4$, which may be identical or different, are each hydrogen, a straight-chained or branched alkyl group with 1 to 6 carbon atoms, a cycloalkyl group with 3 to 6 carbon atoms, a phenyl pyridine or pyrazine group optionally substituted by halogen, methoxy or trifluoromethyl or by a straight-chained or branched alkyl group with 1 to 6 carbon atoms; or, $R^3$ and $R^4$ together with the nitrogen atom to which they are attached form a (ILLEGIBLE) optionally substituted by one or more straight-chained or branched alkyl groups with 1 to 4 carbon atoms, or a physiologically acceptable acid addition salts thereof.

2. A compound of formula I, as claimed in claim 1, wherein,
$R^1$ is a methyl or ethyl group,
$R^2$ is a chlorine-substituted phenyl or pyridinyl group,
$R^3$ is hydrogen or a methyl or ethyl group,
$R^4$ is a lower alkyl group with 1 to 4 carbon atoms or $R^3$ and $R^4$ together with the nitrogen to which they are attached form an N-methyl substituted piperazinyl group.

3. In accordance with claim 1, the compound 4-(5-Chloropyridin-2-yl)-3-methyl-5-[(4-methyl piperazinyl)carbonyl]oxy-1,2,4,-triazole.

4. In accordance with claim 1, the compound 4-(5-Chloropyridin-2-yl)-3-methyl-5-[N-tert.-butylaminocarbonyl]oxy-1,2,4-triazole.

5. In accordance with claim 1, the compound 4-(4-Chlorophenyl)-3-ethyl-5-[(4-methylpiper-azinyl)-carbonyl]oxy-1,2,4-triazole.

6. In accordance with claim 1, the compound 4-(5-Chloropyridin-2-yl)-3-methyl-5-[N,N-diethylaminocarbobonyl]oxy-1,2,4-triazole.

7. In accordance with claim 1, the compound 4-(5-Chloropyridin-2-yl)-3-methyl-5-[N-methylamino-carbonyl]oxy-1,2,4-triazole.

8. In accordance with claim 1, the compound 4-(5-Chloropyridin-2-yl)-3-methyl-5-[N,N-dimethyl-aminocarbonyl]oxy-1,2,4-triazole.

9. In accordance with claim 1, the compound 4-(4-Chlorophenyl-3-methyl-5-[(4-methylpiperazinly)-carbonyl]oxy-1,2,4-triazole.

10. A pharmaceutical composition comprising an effective amount of a compound according to claim 1 and a pharmaceutically acceptable carrier.

* * * * *